United States Patent [19]

Lee

[11] Patent Number: 4,766,761

[45] Date of Patent: Aug. 30, 1988

[54] METHOD OF DETERMINING THE INTERNAL POROSITY OF POWDERS

[75] Inventor: Biing-Lin Lee, Broadview Heights, Ohio

[73] Assignee: The B. F. Goodrich Company, Akron, Ohio

[21] Appl. No.: 92,817

[22] Filed: Sep. 3, 1987

[51] Int. Cl.[4] ............................................ G01N 15/08
[52] U.S. Cl. .......................................... 73/38; 73/866
[58] Field of Search .................................... 73/38, 866

[56] References Cited

U.S. PATENT DOCUMENTS 4,181,023  1/1980  Clamroth et al. ..................... 73/866

OTHER PUBLICATIONS

"The Forces on Obstacles Suspended in Flowing Granular Materials", by T. D. Atkinson, J. C. Butcher, M. J. Izard, & R. M. Nedderman.

"The Theoretical Prediction of Stress Distributions in Hoppers", by R. M. Nedderman.

"The Effect of Vibration on the Rheology of Powders", by B. H. Kaye, J. E. Leblane, D. Moxam, and D. Zubac.

*Primary Examiner*—Stewart J. Levy
*Assistant Examiner*—Hezron E. Williams
*Attorney, Agent, or Firm*—James R. Lindsay; Daniel J. Hudak

[57] ABSTRACT

A method for determining the approximate value of the internal porosity of a powder is set forth wherein a quick determination is achieved by measuring the maximum drawing force of an object such as a plate being withdrawn from within a bed of the powder, and repeating the removal of the object at least one additional time from a more compacted powder bed and utilizing the values obtained to solve simultaneous equations. The process is particularly suitable with regard to determining the internal porosity of polyvinyl chloride powders.

11 Claims, 2 Drawing Sheets

METHOD OF DETERMINING THE INTERNAL POROSITY OF POWDERS

TECHNICAL FIELD

The present invention relates to a method of determining the internal porosity of powders based on low pressure powder rheology by measurement of forces exerted on an object suspended in a bed containing said powder.

BACKGROUND OF THE INVENTION

Heretofore, the internal porosity of fine particles has been determined by mercury intrusion porosimetry, a procedure by which mercury is forced under increasing pressure through a graduated penetrometer into the open pores of a particle sample. The volume of mercury forced into the pores is determined and the interior pore volume can be determined from that measurement. However, this method (ASTM D2873-70) is time-consuming and requires elaborate equipment.

The present invention presents a method of determining internal porosity by measuring forces on an obstacle suspended in a bed containing said powder. The stress distributions in a loosely packed bed of powder have been analyzed, for example, by R. M. Nedderman in "The Theoretical Prediction of Stress Distribution in Hoppers," *Tran. I. Chem. Eng.*, 60,259 (1982), and by Atkinson, et al. in "The Forces on Obstacles Suspended in Flowing Granular Materials," Chem. Eng. Sci. 38, 91 (1983). Nedderman and Atkinson et al. both studied the axial forces applied to an object suspended in a powder medium as the powder flowed by gravity through a funnel outlet out of the powder bed. Other work includes the study of Kaye, et al, on "The Effect of Vibration on the Rheology of Powders", published in a paper presented at a conference entitled "International Powder and Bulk Solids Handling and Processing," held in Atlanta, Ga., May 24-26, 1983, and also an oral presentation of W. K. Lee presented at the 1982 AIChe Annual Meeting held Nov. 14-19, 1982 in Los Angeles, Calif., and at the 57th Annual Meeting of the Society of Rheology Oct. 14-17, 1985 in Ann Arbor, Mich. Kaye et al. recorded the change in the force necessary to draw sandpaper out of a powder bed as the bed is subjected to vibration. Lee studied the force necessary to draw a plate from a loosely packed powder bed as a function of the depth of insertion of the plate.

SUMMARY OF THE INVENTION

It is therefore an aspect of the invention to define an easy and quick method of estimating the internal porosity of a powder. This method involves a determination of a drawing force, that is the force required to draw an object such as a plate vertically embedded in a dry powder bed a suitable distance. The powder is contained in a container of any suitable size or shape such as a cylinder in which the top surfaces of the side walls extend above the top of the powder. The maximum drawing force is related to the strength of a powder bed and also to the degree of packing of the powder.

DETAILED DESCRIPTION

Figure 1:
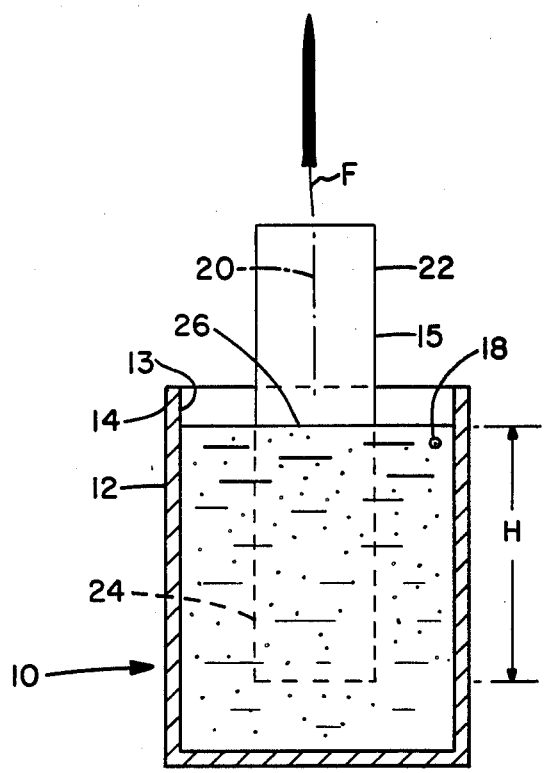
FIG. 1 is a schematic representation of the powder bed in accordance with the invention.

A schematic representation of the concept or setup utilized to determine forces in the present invention is shown in FIG. 1. A powder bed 10 comprises a container 12 which can be any suitable size or shape such as a vertical cylinder of a suitable diameter having an inner surface 13, which is desirably smooth. The container 12 contains a dry powder or granular medium 18, the porosity of which is to be determined. The sides 14 of the container extend above the top surface 26 of the powder medium. The cylindrical container has a vertical central axis 20.

In order to determine the internal porosity of the powder medium 18, a drawing force, denoted generally as F, is measured. The drawing force F is the force necessary to draw an object 15, which is suspended in the powder bed 10, a suitable distance such as through height H. It is preferable that the object 15 is a flat, rectangular plate of thin cross section, although it can be a tube, a rod, or the like.

Object 15 is suspended with one end 24 extending into the powder 18 so that the end is a suitable distance H from the top surface 26 of the powder 18. By the term "a suitable distance H" from the top surface of the powder, it is meant that the depth of the plate inserted into the powder is kept the same with regard to repeated insertions and removals of the object. The remaining end 22 of the object 15 extends beyond the top surface 26 of the powder 18. Although object 15 can generally be located at any position in container 12, it is desirably located in the center of the container as axially aligned with central axis 20 of powder bed 10. In order to determine drawing force F, the object 15 is pulled by a force applied to the top end 22 of the object in an upward or verticle direction which in a desired situation is along central axis 20. The speed at which the plate is withdrawn can be any suitable speed and is the same in all subsequent tests. The actual speed is generally quite low as a fraction of an inch per minute. The force required and especially the maximum force, $F_{max}$, to withdraw the plate is recorded. For example, a force recording apparatus such as an Instron load cell (B-cell) and its force recorder can be utilized.

The effect of packing arrangement of a powder medium on the maximum drawing force was measured utilizing a series of tests with the plate being pulled from various solid fraction powder beds (or external interstitial voidage). The maximum initial drawing force $F_o$ and its corresponding volume $V_o$ are measured and recorded. The object, such as plate 15, is then reinserted into the powdered bed and the powdered bed is then compacted as by applying vibration to or tapping the container. The same depth or height "H" from top surface 26 of the container is maintained as before. In essence, a more compacted or higher bulk density powdered bed is obtained. This procedure is repeated with the maximum drawing force $F_1$ and volume $V_1$ being measured. Subsequent compacting and drawing steps can also be made. The unit of volume, e.g. $V_o$, $V_1$, etc., is expressed as cc/gram. Compacting of the powder bed effects the packing arrangement, expressed as the external void fraction, and significantly alters the effective sustaining strength expressed as the maximum drawing force of a powder bed. The external voidage (E) of a powder bed is changed by compacting, where E is expressed as follows:

$$E(\%) = \frac{\text{volume of external voids}}{\text{total volume of powder bed}}$$

that is, $$E(\%) = \frac{V_E}{V_{BED}} = \frac{V_E}{\frac{1}{pd} + I + V_E}$$

$V_E$ is the volume of the external interstital voids, I is the internal porosity volume, and 1/pd is the volume of the solids. All units are expressed as cc/gram.

The total volume of the powder bed is as follows:

total volume of powder bed = volume of solids + volume of internal porosity + volume of external interstitial voids In mathematical terms, $$V_{BED} = \frac{1}{pd} + I + V_E \quad (1)$$

$V_{BED}$ is a total volume of the powder bed, that is the initial volume $V_o$, or a subsequent compacted volume as for example $V_1$, $V_2$, etc. The term "pd" is the fused density of the powder material.

Figure 2A:
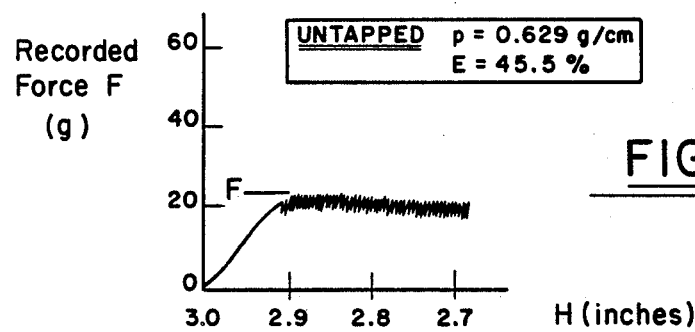
FIG. 2A and FIG. 2B are a graphs of the drawing force as a function of compacted bulk density, or external particle voids.
Figure 2B:
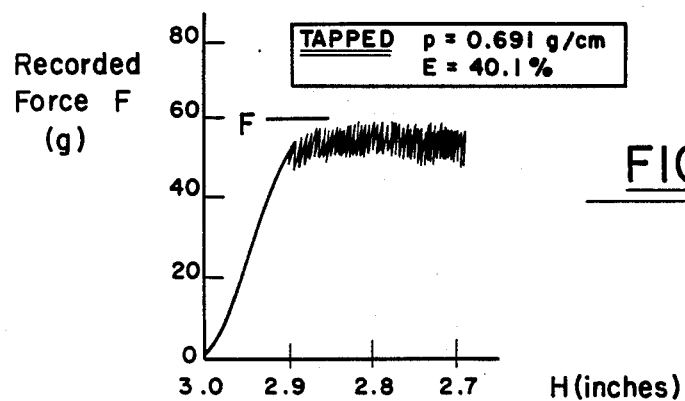

Experimental observations indicate that when a plate is withdrawn from a powder bed, the drawing force increases to a maximum value (F) as shown in FIG. 2. Thereafter, the drawing force has an oscillatory decrease with the amplitude of the oscillation decreasing.

The maximum drawing force is an empirical measurement for the sustaining strength of a powder bed, and is strongly influenced by the packing density or the external interstital void of a powder bed. For a loose, untapped powder bed, a small force is required. Rearrangement of the powder packing, produced by tapping the powders to increase the solid fraction or tapped bulk density of a powder bed, generally produces a maximum drawing force which can be considerably greater than that of a loosely packed powder bed. The maximum drawing force of the untapped and tapped materials studied follows the relation:

$$E_1 - E_0 = -\frac{1}{B} \log \frac{F_1}{F_0} \quad (2)$$

where B is a constant, and E is the external void fraction of a powder bed, and F is its correspondent maximum drawing force. The subscripts o and 1 respectively refer to the untapped and subsequently compacted or tapped condition.

The internal porosity of powder is then calculated by simultaneously solving equations (1) and (2). The result is as follows:

Internal porosity, $I$ (cc/gm) = (3)

$$\left(\frac{1}{B} \log \frac{F_1}{F_0}\right)\left(\frac{V_0 \times V_1}{V_0 - V_1}\right) - \frac{1}{pd}$$

"B" can be estimated using equation (2) and the change in the drawing force data and volumes determined after tapping.

EXAMPLE

The experimental setup used is shown in FIG. 1. The diameter of the cylindrical container was 8.5 cm. A stainless steel plate of width 2.54 cm and thickness 0.076 cm was used. The height of a powder bed was at least 9 cm. The depth to which the plate was inserted into the powder was 7.62 cm and was the same for every test. The speed to withdraw the plate was 0.05 inch/min. The force required to withdraw the plate was continuously recorded using an Instron load cell (B-cell) and its force recorder as shown in FIG. 2, the maximum drawing force is the peak of the curve.

The density of fused powder was determined. A powder bed was set up and the volume $V_o$ was measured and the initial maximum drawing force $F_o$ was determined. The powder bed was tapped and the bed volume $V_1$ and the drawing force $F_1$ were determined. Subsequently, the powder bed was once again tapped, the bed volume $V_2$ and the drawing force $F_2$ were measured. The above equations can be simultaneously solved by utilizing the second set of date. An average value of the internal porosity can be derived from the calculated results. The units of $V_o$, $V_1$, and $V_2$ are expressed as cc/g.

Figure 3:
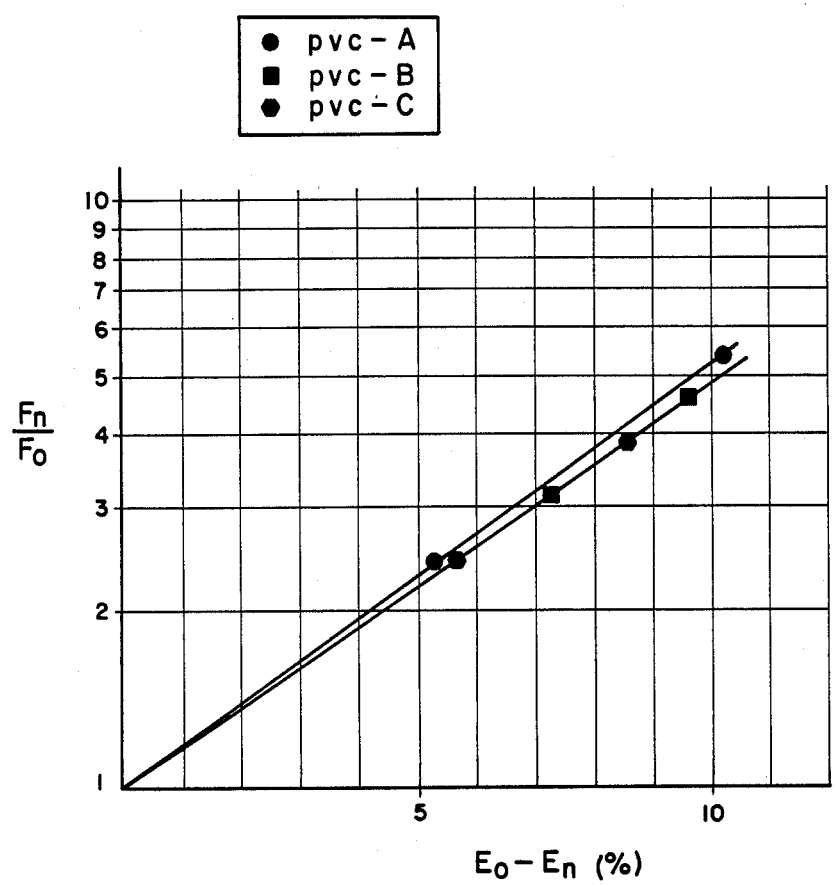
FIG. 3 is a graph of the maximum drawing force ratio of three different polyvinyl chloride powdered resins as a function of the external void.

FIG. 3 shows the experimental results of three (3) different PVC powders, expressed using equation (2), where PVC-A is an Advantage suspension resin, PVC-B is a 103 EP F176 suspension PVC resin, and PVC-C is Geon 92, a high porosity, spherical mass resin. All three resins are manufactured by BFGoodrich. $F_o$ is the maximum drawing force for a loosely packed powder medium without tapping, and $E_o$ is its corresponding external void. Equation (2) appears to hold for these powders for $E_o - E_n < 10\%$. Pertinent data and the estimated internal porosity of these three PVC powdered resins are set forth in the following Table:

|  | PVC-A | PVC-B | PVC-C |
|---|---|---|---|
| Bulk density (g/cc) (ASTM D-1895-61T) | 0.6196 | 0.5611 | 0.4476 |
| Funnel Flow (Sec.) (ASTM D-1895-61T) | 14.25 | 16.25 | 18.10 |
| Average Particle Size (Micron) | 153 | 156 | 270 |
| Estimated Internal Porosity (cc/g) | 0.14 | 0.16 | 0.48 |

The test is relatively quick and can be accomplished in less than ten minutes.

The process is illustrated for use with PVC powders, but may be used for any type of powders utilized in plastics manufacturing, such as compounding powders and incoming PVC powders for chlorination, i.e. for making CPVC or for detergent powders, pharmaceutical powders, and even foodstuffs such as coffee or powdered sugar.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope to the specific embodiment herein shown and described nor in any way that is inconsistent with the extent to which the progress in the art has been advanced by the invention.

What is claimed is:

1. A method of determining an approximate value for the internal porosity I of a powder wherein all units $V_o$, $V_1$, $V_{Eo}$, $V_{E1}$ are expressed as cc/g, comprised of particles having a fused density characterized by pd, comprising the steps of:

(a) determining the fused density pd of said powder;
   (b) forming a powder bed in a container,
   (c) determining for said powder bed an initial volume $V_o$, equaling the volume of said solid 1/pd, the volume of the external voids $V_{Eo}$ and the volume of the internal porosity I;
   (d) suspending at least a portion of a drawing object a depth H in said powder bed and thereafter measuring the initial maximum force $F_o$ necessary to draw said object out of said container,
   (e) compacting said powder bed to change the volume of said powder bed to $V_1$ and said external void volume to $V_{E1}$ by altering the packing arrangements of said particles;
   (f) determining a new volume $V_1$ of said powder bed, equaling the volume of said solid 1/pd, the new volume of the external voids $V_{E1}$ and the volume of the internal porosity I;
   (g) suspending said drawing object to said depth H in said powder bed and thereafter measuring the maximum force $F_1$ necessary to draw said object out of said container, and
   (h) calculating the internal porosity I by simultaneously solving the equations:

$$V_{BED} = \frac{1}{pd} + I + V_E \quad (1)$$

and $$E_1 - E_0 = -\frac{1}{B} \log \frac{F_1}{F_0} \quad (2)$$

to obtain the equation:

$$I \,(cm/gm) = \left(\frac{1}{B} \log \frac{F_1}{F_0}\right)\left(\frac{V_0 \times V_1}{V_0 - V_1}\right) - \frac{1}{pd} \quad (3)$$

wherein B is a constant, F is the maximum drawing force, V is the volume of the powder bed, pd is the fused density of said powder, and the subscripts o and 1 respectively refer to the initial and the subsequent compacted condition.

2. A method of determining an approximate value for the internal porosity of a powder as set forth in claim 1, including the subsequent steps of compacting the powder bed to change the volume fraction of external voids to $E_2$ by altering the packing arrangement of said particles; determining a new volume, $V_2$ for said powder bed; suspending the drawing object a depth H in the powder bed and thereafter measuring the initial maximum force $F_2$ necessary to draw the object out of said container, simultaneously solving the equations using $E_2$, $V_2$, and $F_2$ to calculate I' and averaging I and I' to more closely approximate the value of the internal porosity.

3. A method of determining an approximate value for internal porosity of a powder as set forth in claim 1, wherein said container has a central axis, and wherein said object is drawn out of said container substantially along said central axis.

4. A method of determining an approximate value for the internal porosity of a powder as set forth in claim 1, wherein said container is a vertical cylinder, said vertical container has a central axis, and said object is drawn out of said container substantially along said central axis.

5. A method of determining an approximate value for the internal porosity of a powder as set forth in claim 4, wherein said drawing object is a rectangular plate having a longitudinal axis aligned with the central axis of the container.

6. A method of determing an approximate value for the internal porosity of a powder as set forth in claim 4, wherein said drawing object is a rod having a longitudinal axis aligned with the central axis of the container.

7. A method of determining an approximate value for the internal porosity of a powder as set forth in claim 4, wherein said drawing object is a tube having a longitudinal axis aligned with the central axis of the container.

8. A method of determining an approximate value for the internal porosity of a powder as set forth in claim 1, wherein said powder is a thermoplastic resin.

9. A method of determining an approximate value for the internal porosity of a powder as set forth in claim 1, wherein said powder is polyvinyl chloride.

10. A method of determining an approximate value for the internal porosity of a powder as set forth in claim 1, wherein said powder is freeze-dried coffee.

11. A method of determining an approximate value for the internal porosity of a powder as set forth in claim 1, wherein said powder is sugar.

* * * * *

UNITED STATES PATENT AND TRADEMARK OFFICE
CERTIFICATE OF CORRECTION

PATENT NO. : 4,766,761
DATED : August 30, 1988
INVENTOR(S) : Biing-Lin Lee

It is certified that error appears in the above-identified patent and that said Letters Patent are hereby corrected as shown below:

Column 6, line 3, the formula should read:

$$I \text{ (cc/gm)} = \left(\frac{1}{B} \log \frac{F_1}{F_o}\right) \left(\frac{V_o \times V_1}{V_o - V_1}\right) - \frac{1}{pd} \qquad (3)$$

Signed and Sealed this

Twenty-fourth Day of January, 1989

Attest:

DONALD J. QUIGG

*Attesting Officer*    *Commissioner of Patents and Trademarks*